United States Patent
Griffiths

(10) Patent No.: US 6,506,169 B2
(45) Date of Patent: Jan. 14, 2003

(54) NON-INVASIVE BLADDER PRESSURE MEASUREMENTS

(75) Inventor: Clive Javan Griffiths, High Heaton (GB)

(73) Assignee: Mediplus Limited, Buckinghamshire (GB)

( * ) Notice: Subject to any disclaimer, the term of this patent is extended or adjusted under 35 U.S.C. 154(b) by 31 days.

(21) Appl. No.: 09/849,952

(22) Filed: May 4, 2001

(65) Prior Publication Data

US 2002/0010404 A1 Jan. 24, 2002

Related U.S. Application Data

(63) Continuation of application No. PCT/GB99/03612, filed on Nov. 2, 1999, now abandoned.

(30) Foreign Application Priority Data

Nov. 7, 1998 (GB) ............................................. 9824333

(51) Int. Cl.$^7$ ................................................ A61B 5/00

(52) U.S. Cl. ........................ 600/584; 600/573; 604/322; 128/885

(58) Field of Search .................................. 600/573, 579, 600/584; 604/317, 322; 128/885

(56) References Cited

U.S. PATENT DOCUMENTS

| | | | | |
|---|---|---|---|---|
| 3,511,241 A | | 5/1970 | Lee .............................. | 128/295 |
| 3,523,522 A | * | 8/1970 | Whitehead et al. .......... | 600/584 |
| 3,769,497 A | * | 10/1973 | Frank .......................... | 600/584 |
| 4,532,936 A | * | 8/1985 | LeVeen et al. ............... | 600/584 |
| 5,377,101 A | * | 12/1994 | Rollema ....................... | 600/584 |
| 5,616,138 A | * | 4/1997 | Propp .......................... | 604/317 |
| 5,807,278 A | | 9/1998 | McRae ........................ | 600/579 |
| 5,823,972 A | * | 10/1998 | McRae ........................ | 600/573 |

OTHER PUBLICATIONS

L P McRae et al, "Non–invasive quantitative method for measuring isovolumetric bladder pressure and urethral resistance in the male", Neurourology and Urodynamics 14: pp. 101–141, 1995.

W Shaefer, "Urethral Resistance? Urodynamic concepts of physiological and pathological bladder outlet function during voiding," Neurourology and Urodynamics 4: pp. 161–201, 1985.

D J Griffiths, "Urodynamics: the mechanics and hydrodynamics of the lower urinary tract," Medical Physics Handbooks 4, Adam Hilger Ltd, Bristol, 1980.

W Schäfer et al, "Non–invasive pressure/flow measurement for precise grading of bladder outflow obstruction," Abstracts of J. Urol. 151, p. 323A, 1994.

D M Gleason et al, "Non–invasive urodynamics: A study of male voiding dysfunction," Neurourology and Urodynamics 16: pp. 93–100, 1997.

B Rikken et al, "Non–invasive bladder pressure measurement. Does the interruption of flow–rate inhibit voiding?," Neurourology and Urodynamics 17, pp. 302–304, 1998.

(List continued on next page.)

Primary Examiner—John Rivell
(74) Attorney, Agent, or Firm—Renner, Otto, Boisselle & Sklar, LLP

(57) ABSTRACT

A method and apparatus for carrying out non-invasive urodynamics investigations on male patients, by controlling urethral pressure, which facilitates diagnosis of, and distinction between, obstructive and non-obstructive voiding dysfunction. A pneumatic cuff (2) is placed around the penis (3) and after commencement of urine flow through the penis, the cuff is automatically inflated over a period of time in order to gradually occlude the urethra before voiding of the bladder is complete. A relationship between the urine flow and the cuff pressure applied is established and this is used to determine a pressure measurement related to the bladder pressure under isovolumetric conditions.

21 Claims, 11 Drawing Sheets

OTHER PUBLICATIONS

P J McCahy et al., "Clinical applicability of non-invasive pressure flow," Klinishe Fysica 4: pp. 4–16, 1997.

R. van Mastrigt, "Non-invasive bladder pressure measurement. Methodology and reproducibility.", Neurourology and Urodynamics 14: pp. 480–481, 1995.

J J M Pel et al., "Non-invasive diagnosis of infravesical obstruction in male patients," Neurourology and Urodynamics 17: pp. 394–395, 1998.

* cited by examiner

NON-INVASIVE BLADDER PRESSURE MEASUREMENTS

This is a continuation of International Application PCT/GB99/03612, with an international filing date of Nov. 2, 1999, now abandoned.

The present invention relates to methods and apparatus for carrying out non-invasive urodynamics investigations on male patients, and in particular to methods and apparatus for controlling urethral pressure and making measurements of bladder pressure, in order to, for example, facilitate diagnosis of, and distinction between, obstructive and non-obstructive voiding dysfunction.

In the past, urodynamics investigations have been carried out using invasive techniques using, for example, catheters introduced into the bladder. Such catheters can be used for both filling the bladder and directly measuring pressure within the bladder, allowing a comprehensive assessment to be made. However, such invasive techniques are associated with severe patient discomfort, a degree of morbidity, and high cost both in financial terms and in time.

It is found that a proportion of men undergoing prostatectomy do not get the anticipated benefit therefrom and many urologists believe all men should have a urodynamics study beforehand to help identify those less likely to benefit from surgery. There is a real need for a simple, easily administered, atraumatic test which will provide information similar to that currently only available from a full urodynamics study, to give objective evidence of obstruction.

A number of prior art techniques have been proposed for non-invasive measurements on male patients. Many of these suggest the use of a condom catheter, having a stop valve and pressure measurement port, which fits over the penis and can be used to make pressure and flow rate measurements under "interrupted flow" or isovolumetric conditions. Such devices are often associated with problems of erroneous measurements arising from leakage and distortion or high compliance of the device, and can be awkward and messy to use.

In another prior art approach, as described in Neurourology and Urodynamics 14:101–114 (1995) "Non-invasive Quantitative Method for Measuring Isovolumetric Bladder Pressure and Urethral Resisance in the Male", L P McRae et al, it has been suggested to use an inflatable cuff around the penis which is initially pressurised to occlude the urethra. The patient then attempts to void so that the urethra above the occluding cuff becomes distended with urine and the static intraurethral pressure proximal to the cuff is related to the maximum isovolumetric bladder pressure. The cuff is then gradually deflated until urinary flow commences, at which point the cuff is rapidly deflated to enable volume and flow rates to be measured. Cuff pressure at the point of first urine passage can be used to assess isovolumetric bladder pressure at the commencement of voiding. No further estimate of bladder pressure is made during the subsequent voiding cycle.

Such a technique can be susceptible to a number of disadvantages. Only a single estimate of bladder contraction is made, which is at the start of the voiding cycle and is based on the occurrence of an event which can be unreliable. No further measurements are obtained to assess how well the bladder contraction is sustained during the rest of the voiding cycle. The measurement is prone to false starts due to transient events such as straining and contraction of the external sphincter which might lead to an erroneous result. It will not always be apparent that this has occurred.

The cuff pressure must initially be elevated to a high level before. commencing the test. For many subjects, this may be higher than necessary and could cause problems.

Many patients with symptoms of obstruction can have hesitation and difficulty initiating voiding. This can make identification of the best time to start reducing the pressure difficult.

It is an object of the present invention to provide a method and apparatus. for carrying out urodynamics studies on male patients.

It is a further object of the present invention to provide a method and apparatus for carrying out a new type of urodynamics study on male patients which provides valuable information previously only available from catheterisation and a conventional urodynamics study, but achieving this with a well tolerated, easily repeated, quick to perform, non-invasive test.

It is a further object of the invention to provide a method and apparatus for obtaining measurements of flow rate during application of a controlled increase in pressure in a penile cuff leading to a reliable measurement of bladder isovolumetric contraction pressure or other rodynamics parameter. Preferably, this can be applied a number of times during the voiding cycle.

According to one aspect, the present invention provides a method of making urethral pressure measurements on a male body comprising the steps of: attaching a pneumatic cuff around the penis; after commencement of urine flow through the penis, automatically inflating the cuff over a period of time in order to gradually occlude the urethra before voiding of the bladder is complete; establishing a relationship between the urine flow and the, cuff pressure applied; and using said established relationship to determine a pressure measurement related to the urethral pressure under isovolumetric conditions.

According to another aspect, the present invention provides an apparatus for making urethral pressure measurements on a male body comprising: a pneumatic cuff adapted to fit around the penis; means for automatically inflating the cuff over a period of time during voiding of the bladder through the urethra in order to gradually occlude the urethra before voiding of the bladder is complete; and means for determining the cuff pressure at which the urethra becomes completely occluded.

According to another aspect, the present invention provides an apparatus for making urethral pressure measurements on a male body comprising: a pneumatic cuff adapted to fit around the penis; means for automatically inflating the cuff over a period of time during voiding of the bladder through the urethra in order to gradually occlude the urethra before voiding of the bladder is complete; means for recording volume of urine flow and cuff pressure as a function of time; means for establishing, from said means for recording, a relationship between urine flow rate and cuff pressure; and means for determining, from said relationship, information about the relationship between bladder contraction and outlet function. In a preferred arrangement, the information may include a measure of outflow resistance.

According to another aspect, the present invention provides an apparatus for making urethral pressure measurements on a male body comprising:

a pneumatic cuff adapted to fit around the penis; means for automatically inflating the cuff over a period of time during voiding of the bladder through the urethra in order to gradually occlude the urethra before voiding of the bladder is complete; means for recording volume of urine flow and cuff pressure as a function of time; means for establishing, from said means for recording, a relationship between urine flow rate and cuff pressure; and means for determining, from said relationship, a measurement related to at least one of: isovolumetric bladder pressure, a minimum value for the contraction pressure at maximum flow, and the opening pressure of a compressive flow controlling zone.

According to another general aspect, the present invention provides an apparatus for controlling urethral pressure on a male body comprising: a pneumatic cuff adapted to fit around the penis; means for automatically inflating the cuff over a period of time during voiding of the bladder through the urethra in order to gradually occlude the urethra before voiding of the bladder is complete; and means for determining the cuff pressure at which the urethra becomes completely occluded.

Embodiments of the present invention will now be described by way of example with reference to the accompanying drawings in which.

Figure 1:
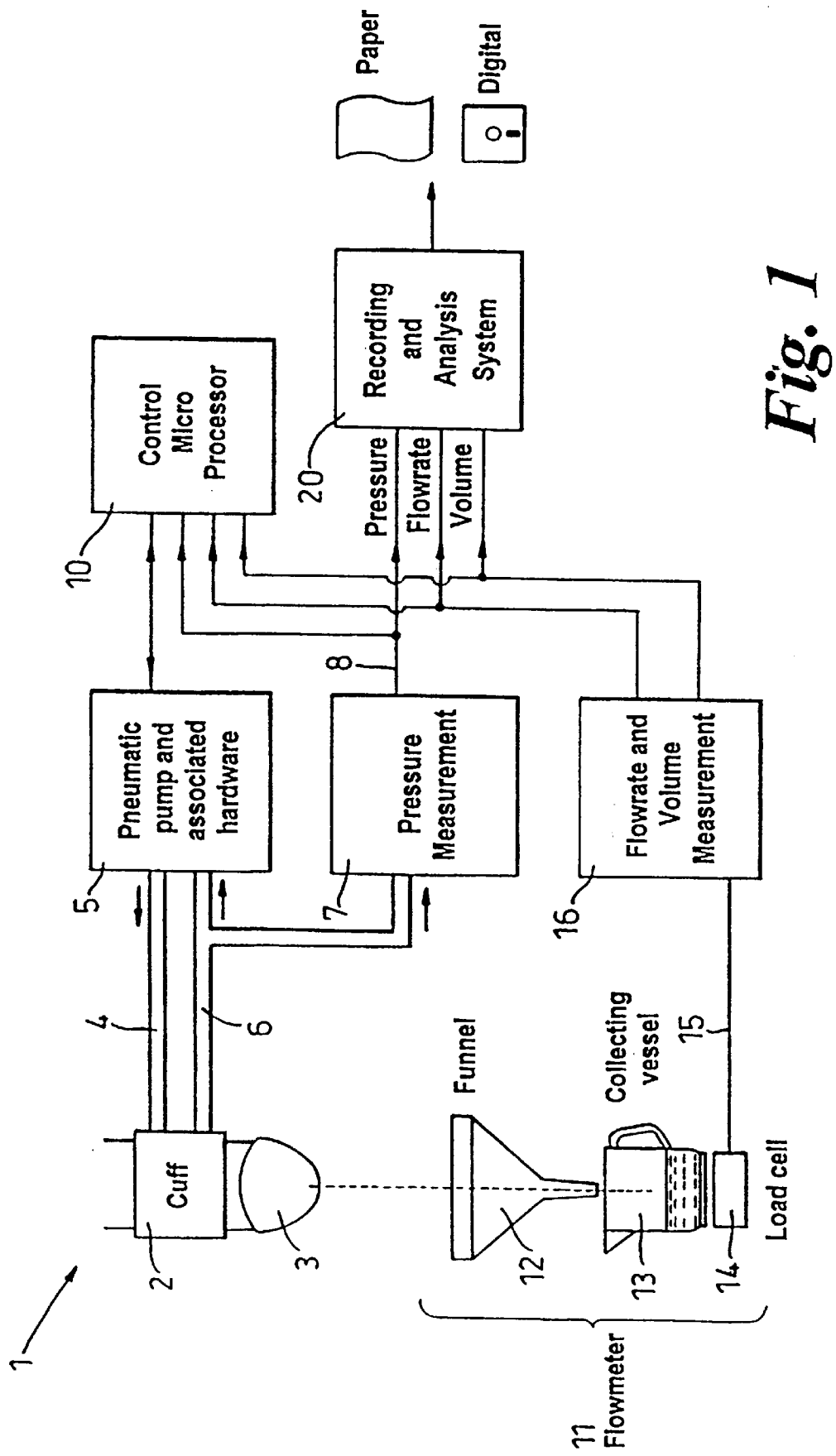
FIG. 1 shows a schematic block diagram illustrating electrical elements of a non-invasive bladder pressure measurement system according to the present invention.

With reference to FIG. 1, there is shown a schematic diagram of the main components of a non-invasive bladder pressure measurement system 1 according to one embodiment of the invention.

A pneumatic cuff 2, operable on similar principles to those used in blood pressure measurement, is applied to the patient's penis 3. The pneumatic cuff 2 preferably has two communicating pneumatic tube connections 4, 6. The cuff is inflatable through a first tube 4 connected to a pneumatic pump system 5 which may be constructed according to principles well established in blood pressure measuring devices, and which is adapted to allow a controlled incremental pressure to be applied to the cuff. A second tube 6 communicates with a pressure sensing device 7 which has an output, preferably adapted to provide digitised, sampled measurements at predetermined time intervals, suitable for direct transfer to the input of a microprocessor-based recording and analysis system 20.

A urine collection mechanism 11 preferably comprises a funnel 12 or other guide and collection vessel 13 with an electrical output for determining volume and flow rate. In the preferred embodiment shown, the collection vessel comprises a weighing device 14 which provides a weight output 15 which is connected to a volume and flow rate measurement module 16. The volume and flow rate measurement module 16 is adapted to calculate urine volume as a function of time and provide digitised flow rate and volume measurements to the microprocessor-based recording and analysis system 20.

The pneumatic pump system 5, pressure sensing device 7, volume and flow rate measurement module 16 and recording and analysis system 20 may all be coupled to a control microprocessor 10 to co-ordinate the functions of the various parts. It will be understood that the control microprocessor 10 and the recording and analysis system 20 may be provided as a suitably programmed computer, or by customised hardware.

Data output from the recording and analysis system 20 may be provided on any suitable output device such as VDU monitor, printer or disk.

Figure 2:
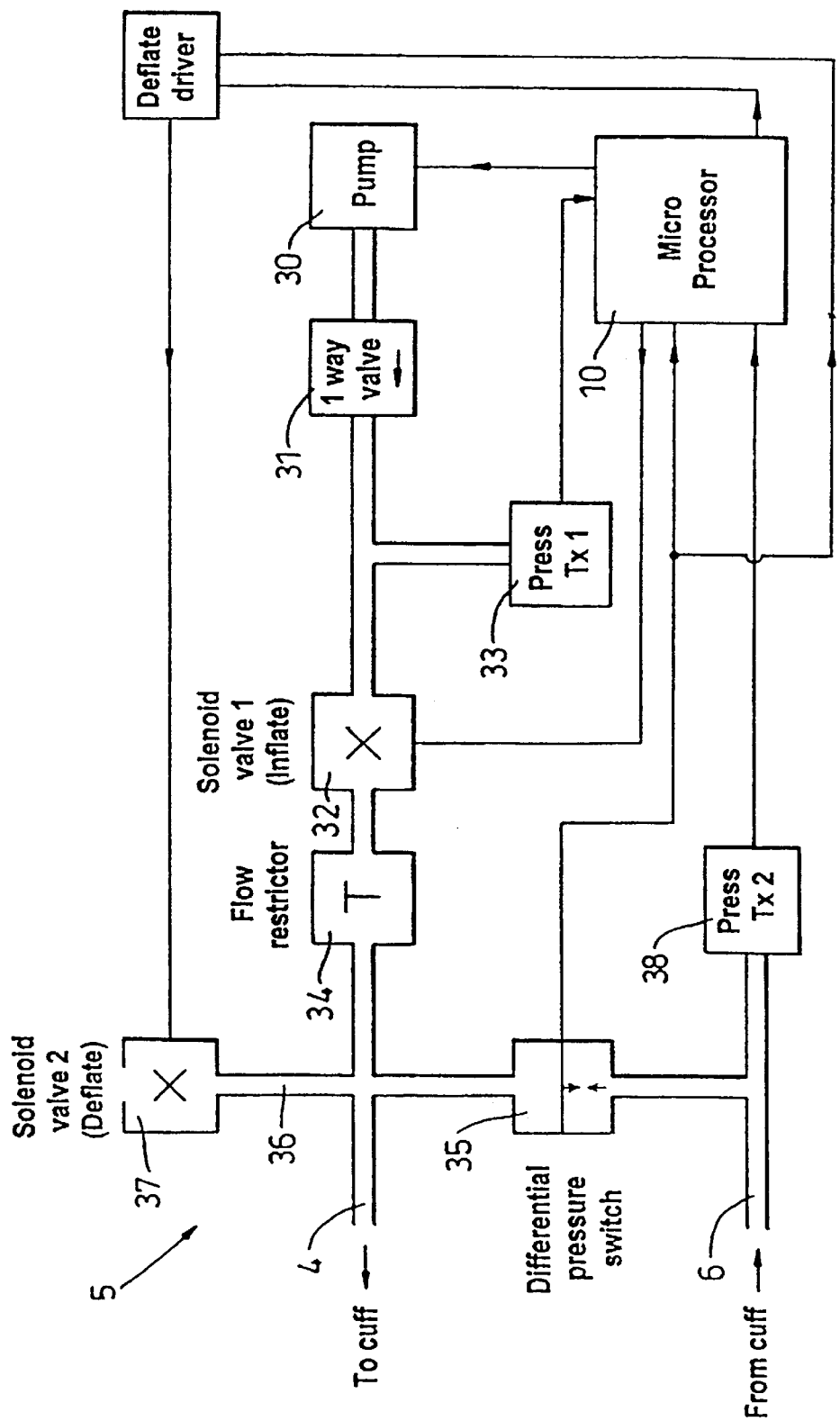
FIG. 2 shows a schematic block diagram illustrating pneumatic elements of the non-invasive bladder pressure measurement system of FIG. 1.

Referring now to FIG. 2, further details of a preferred pneumatic system forming the main components of pneumatic pump system S and control microprocessor 10 of FIG. 1 are described.

A pump 30 provides for the pressurisation of the system via a one way valve 31 and solenoid valve 32. In a preferred embodiment, the pump provides an air reservoir upstream of the solenoid valve 32 at approximately 300 cmH$_2$O pressure. A pressure transducer 33 provides feedback of this pump pressure upstream of the solenoid valve 32 to control the pump 30.

Downstream of the solenoid valve 32 a flow restrictor 34 prevents over-inflation of the cuff 2 which is connected, by the inflation tube 4, to the downstream side of the solenoid valve 32 and flow restrictor 34. The second tube 6 is connected to a pressure sensing device 38. A differential pressure switch 35 provides for communication between the first and second tubes as a safety device in the event of blockage within the cuff 2 or one of the tube connections 4, 6.

The cuff and pneumatic system is connected to a depressurisation line 36 connected to a second solenoid valve 37. The pump 30 and solenoid valves 32, 37 are under the control of microprocessor controller 10, which may also be connected to receive signals from the pressure transducers 33, 7. For ensuring safety, the pressure in the cuff is restricted to a suitable maximum, eg. 200 cmH$_2$O, in the preferred embodiment.

Figure 3:
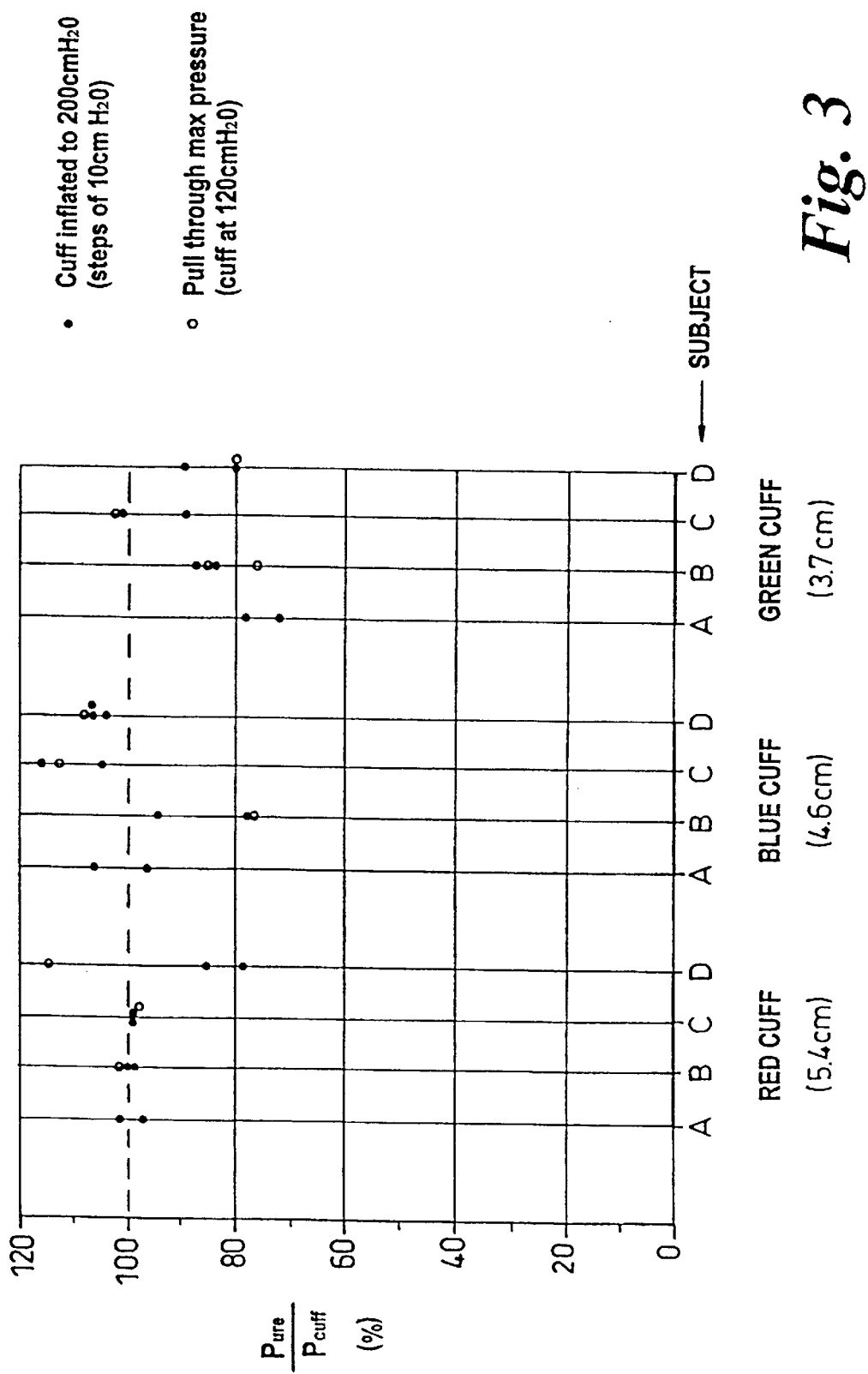
FIG. 3 shows a graph of urethral pressure against cuff pressure as a percentage, for varying cuff widths and for different subjects.

In the preferred embodiment, the cuff should have a width exceeding the diameter of the penis. In comparative tests using pressure transducers, pressure measurements were made using cuff widths of 3.7 cm, 4.6 cm and 5.4 cm. Using the widest practicable cuff has been demonstrated to produce the most consistent measurements. Illustrative results for four patients, showing urethral pressure ($P_{ure}$) against cuff pressure ($P_{cuff}$) as a percentage and for varying cuff widths are shown in FIG. 3.

In operation, the bladder pressure measurement system 1 is adapted to obtain a series of measurements of the volume of urine passed and the cuff pressure, as a function of time, over a period during which (a) the patient commences voiding of the bladder with the cuff deflated, and (b) the pump 30 commences gradual inflation of the cuff 2 until urine flow is stopped. The cuff pressure is then plotted as a function of flow rate to produce a relationship therebetween.

Preferably, the cuff is inflated in incremental steps of, for example, 10 cmH$_2$O and pressure measurements are made between each increment. In the preferred embodiment, the incremental steps last for between 0.5 sec and 1.0 sec, with a preferred value of approximately 0.75 sec. However, a continuously variable rate of inflation may be used if appropriate.

The optimum rate for incremental increase depends in part upon the speed of response of the flow meter 11, 16 and also on the proximal impedance and the compliance of the urethra. When the duration of voiding permits, the inflation/deflation cycle is preferably repeated as many times as possible. In the group of patients for whom the test is most appropriate, voiding is usually sufficiently prolonged to perform three or more cycles.

The technique relies on two assumptions. Firstly, if, while the bladder is emptying, the stream is interrupted by introducing a blockage, then once stasis is established the pressure in the urethra proximal to the blockage equates to the bladder pressure, apart from the hydrostatic height difference between the bladder and the cuff. Simultaneous fluoroscopy has shown the urethra to remain open and pressure measurement within the urethra has shown this assumption to be valid.

Secondly, when blockage is caused by inflation of a cuff around the penis, it is assumed that the pressure in the cuff is transmitted to the walls of the penile urethra and that when this exceeds the bladder pressure, flow is interrupted. This is similar to the assumption made when blood pressure is routinely measured. This assumption has been assessed by simultaneous penile urethral pressure measurements as illustrated in FIG. 3.

Figure 4:
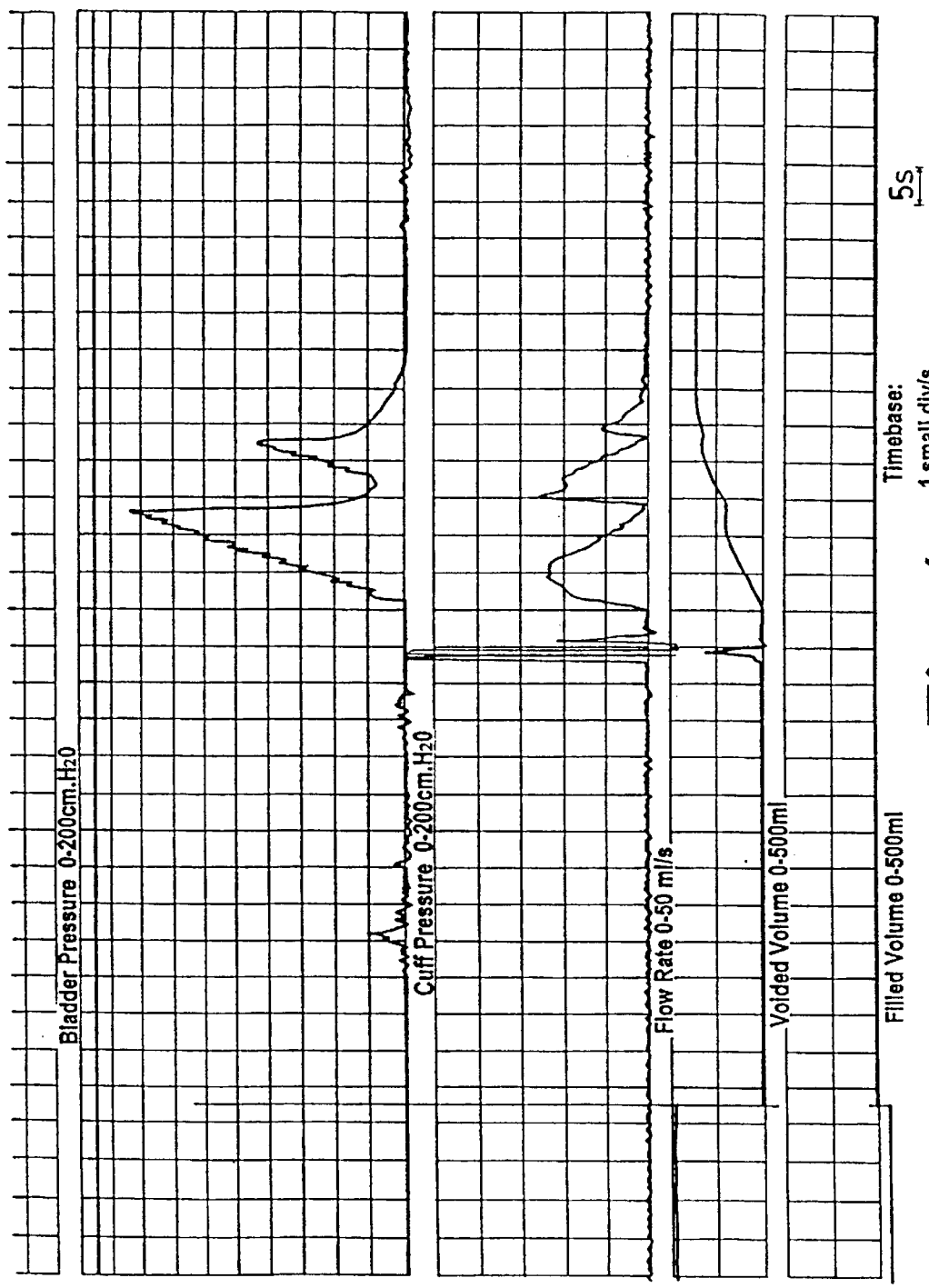
FIG. 4 shows a graph of cuff pressure and flow rate against time for a healthy subject.
Figure 5:
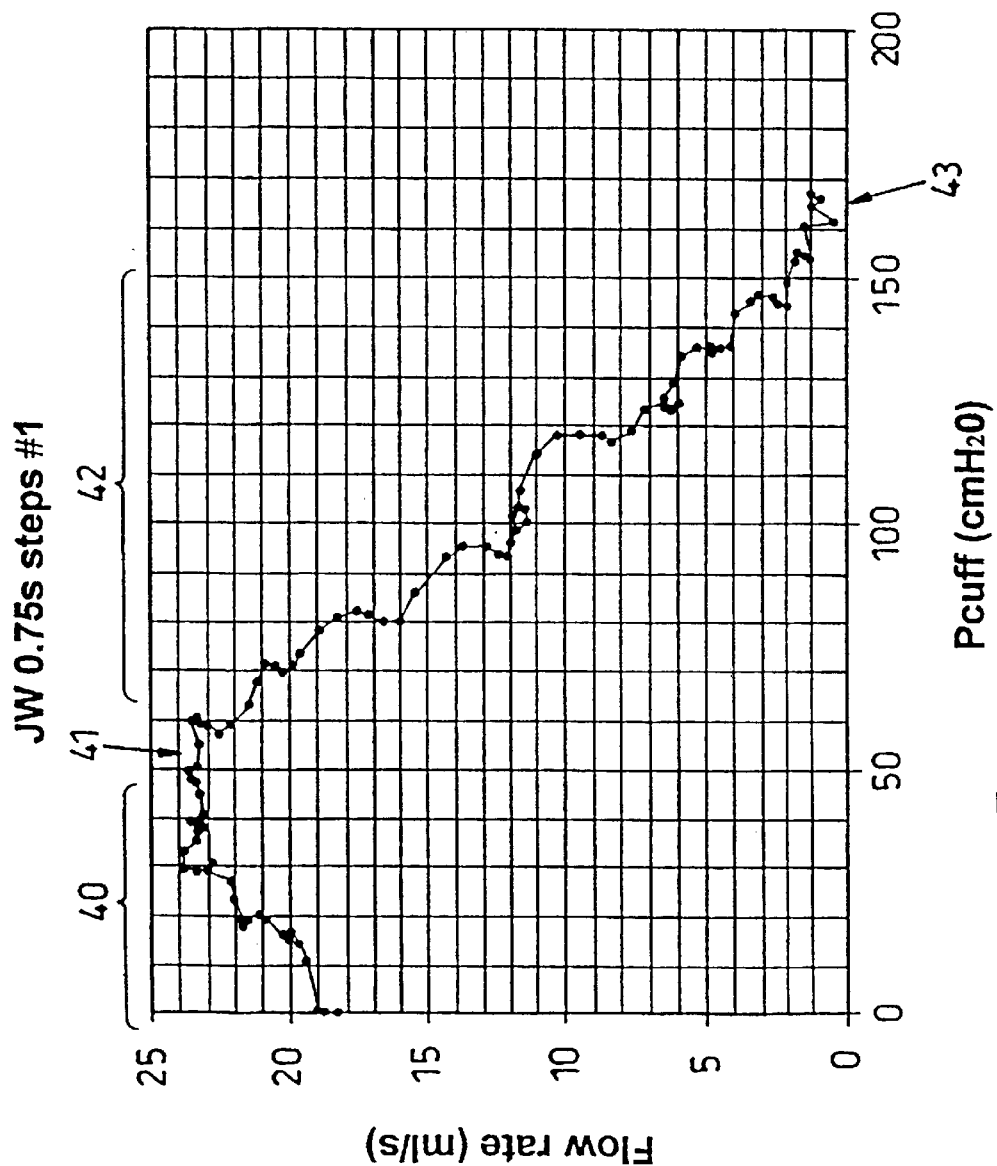
FIG. 5 shows a plot of flow rate against cuff pressure from the data of FIG. 4.

FIG. 4 illustrates the cuff pressure and the flow rate against time for a healthy volunteer. FIG. 5 shows the resultant X-Y plot of flow rate against cuff pressure. A correction has been applied to compensate for the delay in the flow rate recording. This delay is partly due to the mechanical delay of the collecting system and partly due to the electronic filter in the flow meter.

Four distinct features can be identified in this graph. Firstly, a plateau region 40 is defined where the cuff pressure increases without reducing the flow rate. Secondly, when the distal resistance imposed by the cuff exceeds a certain level it starts reducing the flow rate and a "knee" point 41 is reached which indicates this. This is the point at which the cuffed region of the urethra takes over as a flow controlling zone. Thirdly, this knee point is followed by a steady, usually linear decrease in flow rate as the cuff pressure is increased, representing the cuff flow controlling zone, shown at 42. Fourthly, the line intersects the pressure axis when the flow rate has been reduced to zero at 43. This point represents the estimate of isovolumetric bladder contraction pressure.

Thus, following the method of the present invention, using the measurement system 1 under the control of microprocessor 10, a recording is made of the flow rate and the cuff pressure in the recording and analysis system 20, and an appropriate correction for the delay in the flow rate recording is applied. The X-Y plot of flow rate versus cuff pressure is produced. From this X-Y plot, the isovolumetric pressure where the slope intercepts the X axis at point 43 is calculated. In addition, the "knee" pressure 41 can be determined which represents a minimum for the contraction pressure at maximum flow. In addition, the cuff pressure for when the flow is reduced to 50%, in the region 42, is used as an empirical measurement relating to bladder contraction and outlet function. Such may be useful in determining outflow resistance.

The "knee" pressure 41 has also been determined to correspond to an important new urodynamics parameter in its own right. Consistent with the work of W Schaefer ("Urethral resistance? Urodynamic concepts of physiological and pathological bladder outlet function during voiding", *Neurourology and urodynamics* 4: pp161–201) and D J Griffiths ("Urodynamics: the mechanics and hydrodynamics of the lower urinary tract", *Medical Physics Handbooks* 4, Adam Hilger Ltd), this "knee" pressure can be equated with the opening pressure of a compressive flow controlling zone. In an obstructed male, this is usually the prostate gland. The test result is therefore capable of providing information about outlet function as well as bladder contraction.

The method of the present invention thereby offers a number of advantages not found in the prior art methods, summarised below.

a) The use of the decreasing flow rate versus cuff pressure graph provides a much more reliable measurement of the isovolumetric bladder pressure than do the measurement techniques using a potentially erroneous single measurement at the start of flow.

b) The test is applied after voiding starts which avoids any problems associated with false starts.

c) The pressure flow plot allows complex voiding patterns to be recognised by the skilled clinician.

d) The method can be applied repeatedly at intervals during the course of voiding to assess how well the bladder contraction is sustained.

e) The transient rise in flow rate after the pressure in the cuff is released can also be used in a similar way to that proposed in the prior art methods, in addition to any measurements made according the steps identified above. Further, by comparison, the efficacy of the initial flow rate is indicated.

f) The cuff pressure at the "knee" of the curve is believed to represent a useful measure of the minimum for the bladder pressure at peak flow and is equated to the opening pressure of a compressive flow controlling zone, often the prostate gland.

g) The cuff pressure at which the flow is reduced to 50% is an empirical measurement which relates to the relationship between bladder contraction and outlet function.

h) Evidence suggests that, for some patients, as the cuff pressure is incremented, there is a temporary reduction in, and then recovery of, flow rate. This is consistent with a small expansion of the proximal urethra because of its compliance each time the cuff pressure increases. This is most apparent when using a flow meter which gives a high frequency response. There is therefore additional information to be gained on the relationship between bladder contraction and outlet function by the use of a flow metering system in which mechanical delay (from the collection system) and electronic delay (from any signal processing such as filtering etc.) are minimised as far as possible.

i) The test is less dependent on the patient's co-operation, and therefore less susceptible to variation.

Figure 6:
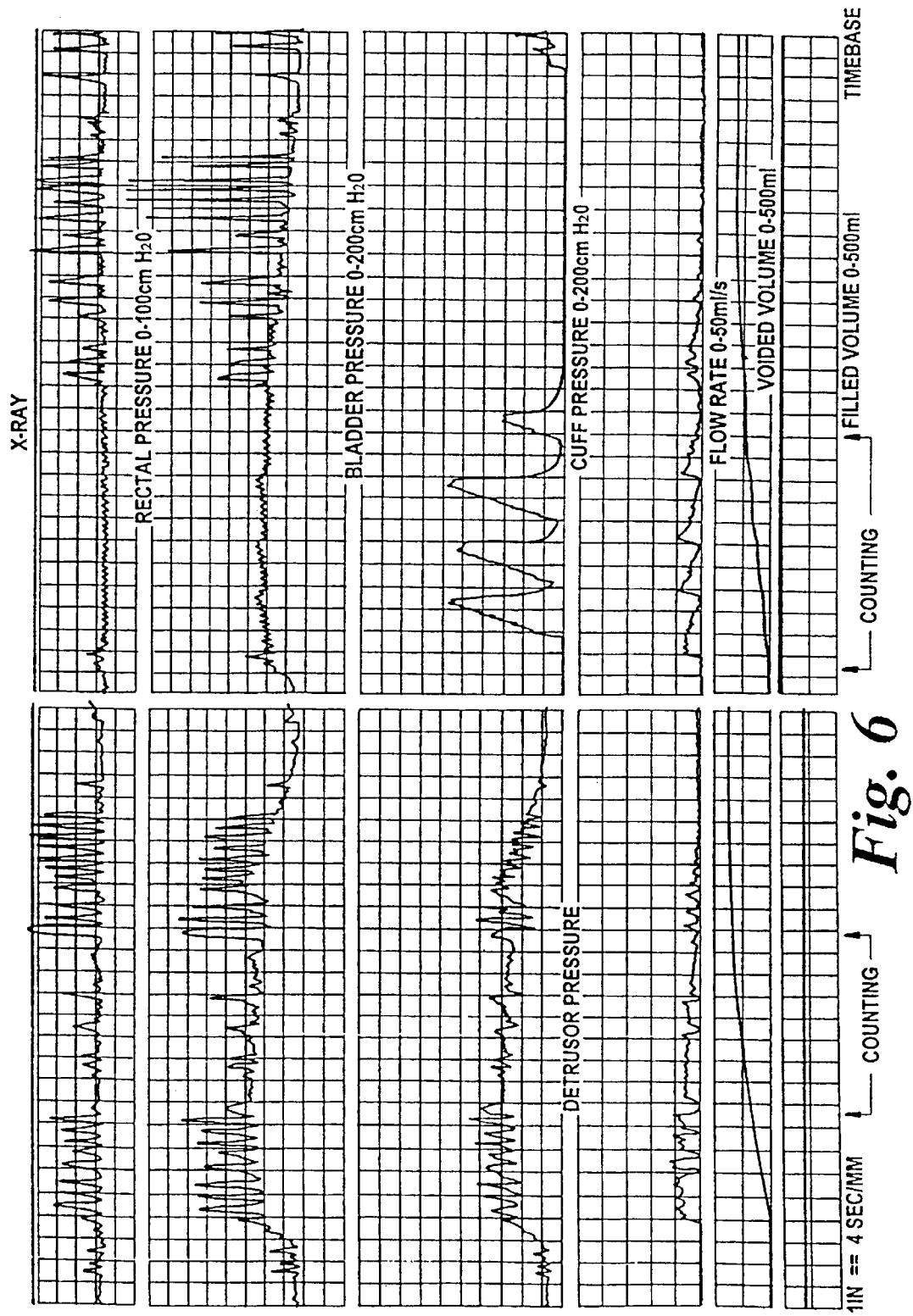
FIG. 6 shows a series of graphs of rectal pressure, bladder pressure, detrusor pressure or cuff pressure and flow rate plotted against time, for a conventional invasive test on the left, and for a non-invasive method of the present invention on the right.

FIG. 6 shows simultaneously recorded rectal pressure, bladder pressure, flow rate, voided volume and filled volume during uninterrupted voiding (on the left half of the figure) and, with detrusor pressure replaced by cuff pressure, during application of the new test (on the right half of the figure). This is for a patient with so called "low pressure, low flow". This also illustrates how asking the patient to count can reduce abdominal straining.

Figure 7:
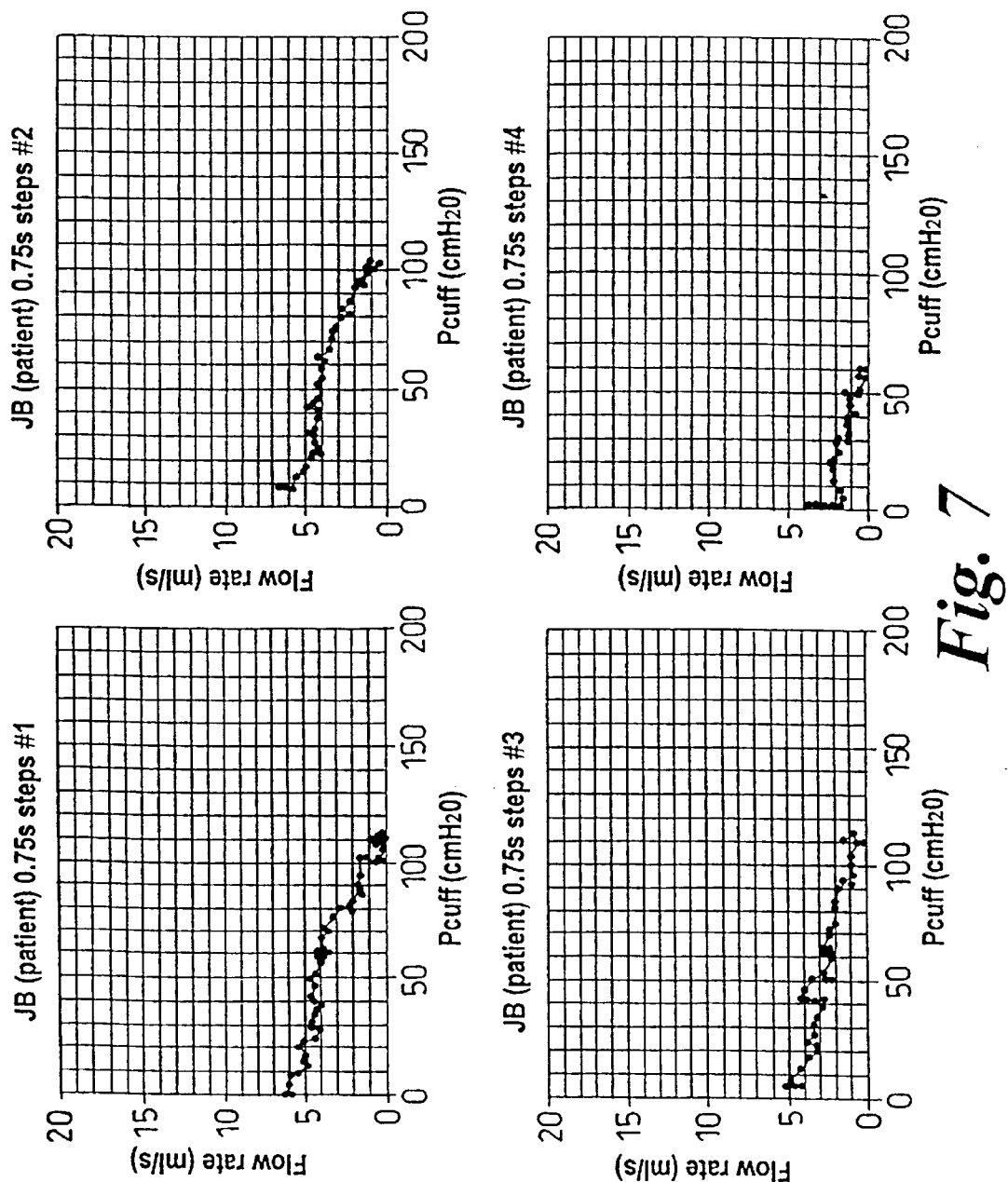
FIG. 7 shows plots of flow rate against cuff pressure from the data of FIG. 6, for each of the four interruptions.

FIG. 7 shows the plot of flow rate against cuff pressure for the patient of FIG. 6, for each of the four interruptions. Note that normally the fourth interruption would be discounted because the flow rate does not recover after deflation of the cuff.

Figure 8:
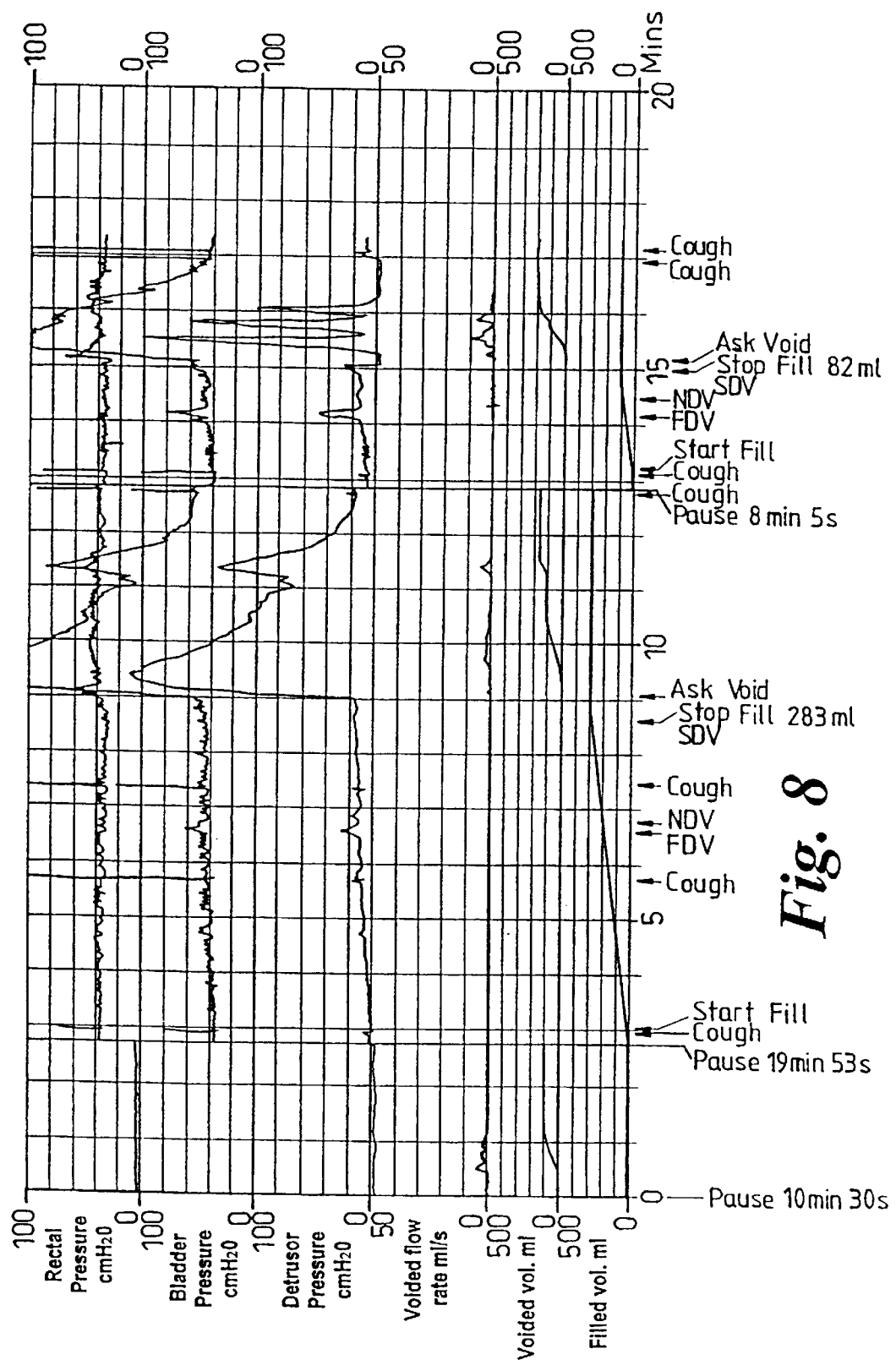
FIG. 8 shows results from a full urodynamic study for a patient with high pressure, low flow voiding condition.

FIG. 8 is a full urodynamics recording for a patient with "high pressure, low flow" voiding, with the new test applied towards the end after refilling the bladder. Note the very high initial contraction which is not sustained, the pattern being detected by the decreasing cuff pressure needed to stop the flow.

Figure 9:
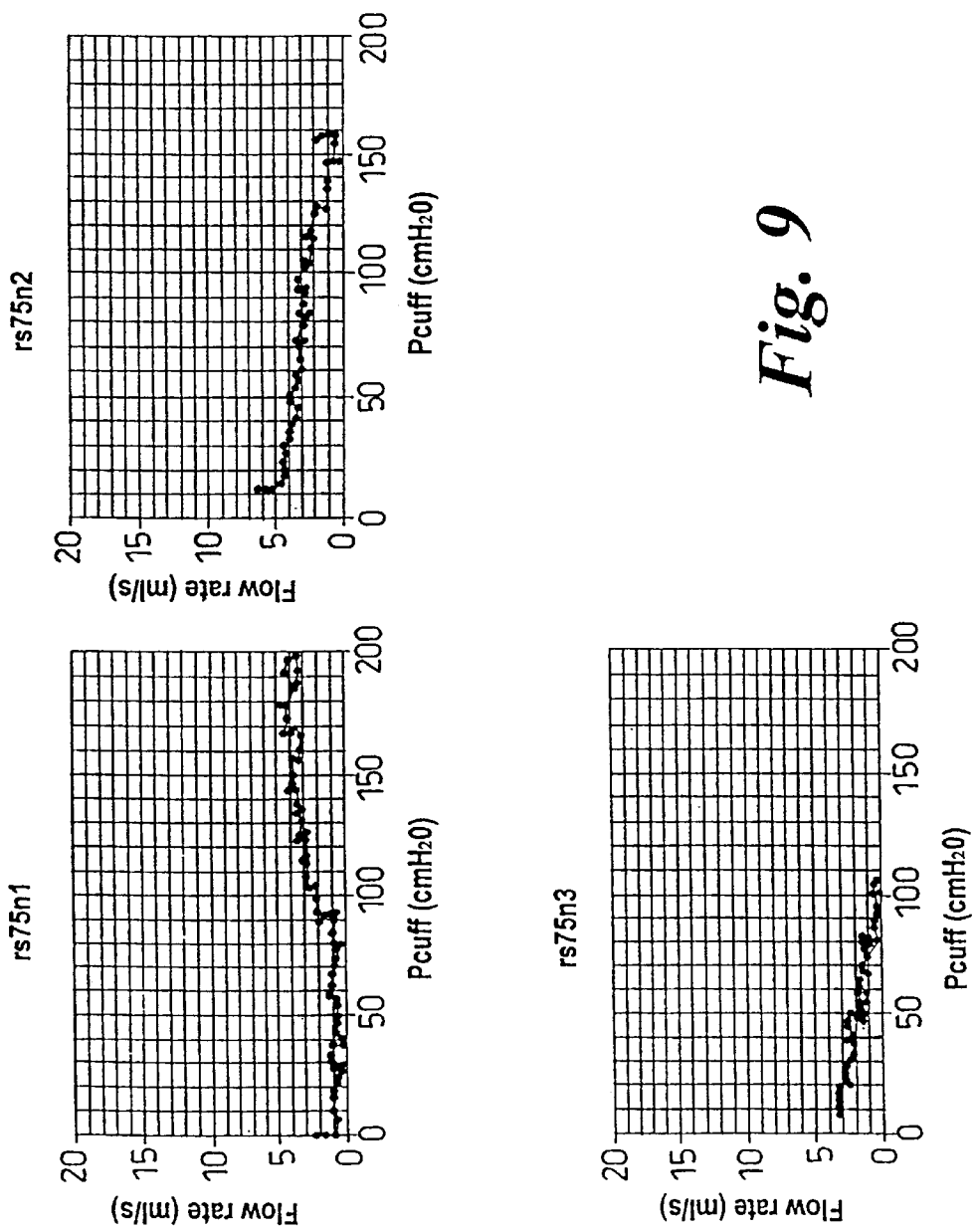
FIG. 9 shows plots of flow rate against cuff pressure from the data of FIG. 8 for each of the interruptions.

FIG. 9 is the plot of flow rate against cuff pressure for this patient for each of the three interruptions. Notice how for the first interruption, flow continues even when the maximum cuff pressure of 200 cMH$_2$O is applied.

Figure 10:
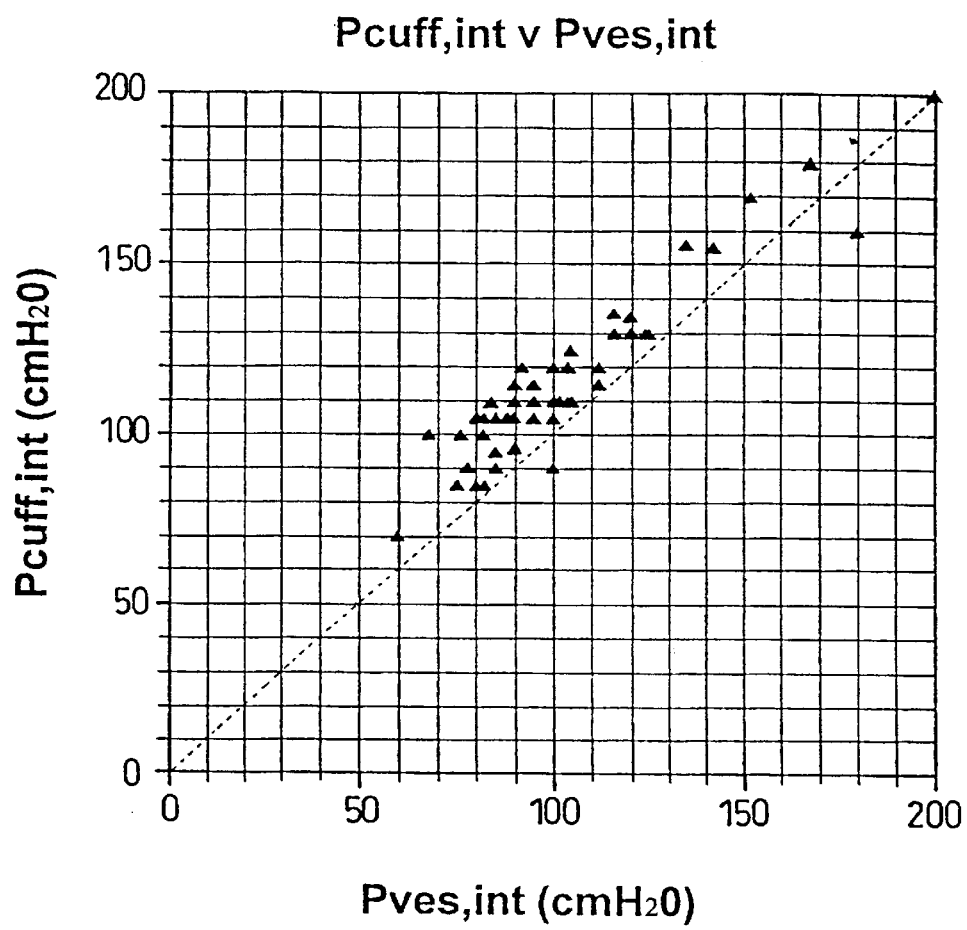
FIG. 10 shows a graph comparing pressure data gathered using conventional invasive techniques with those gathered using the present invention.
Figure 11:
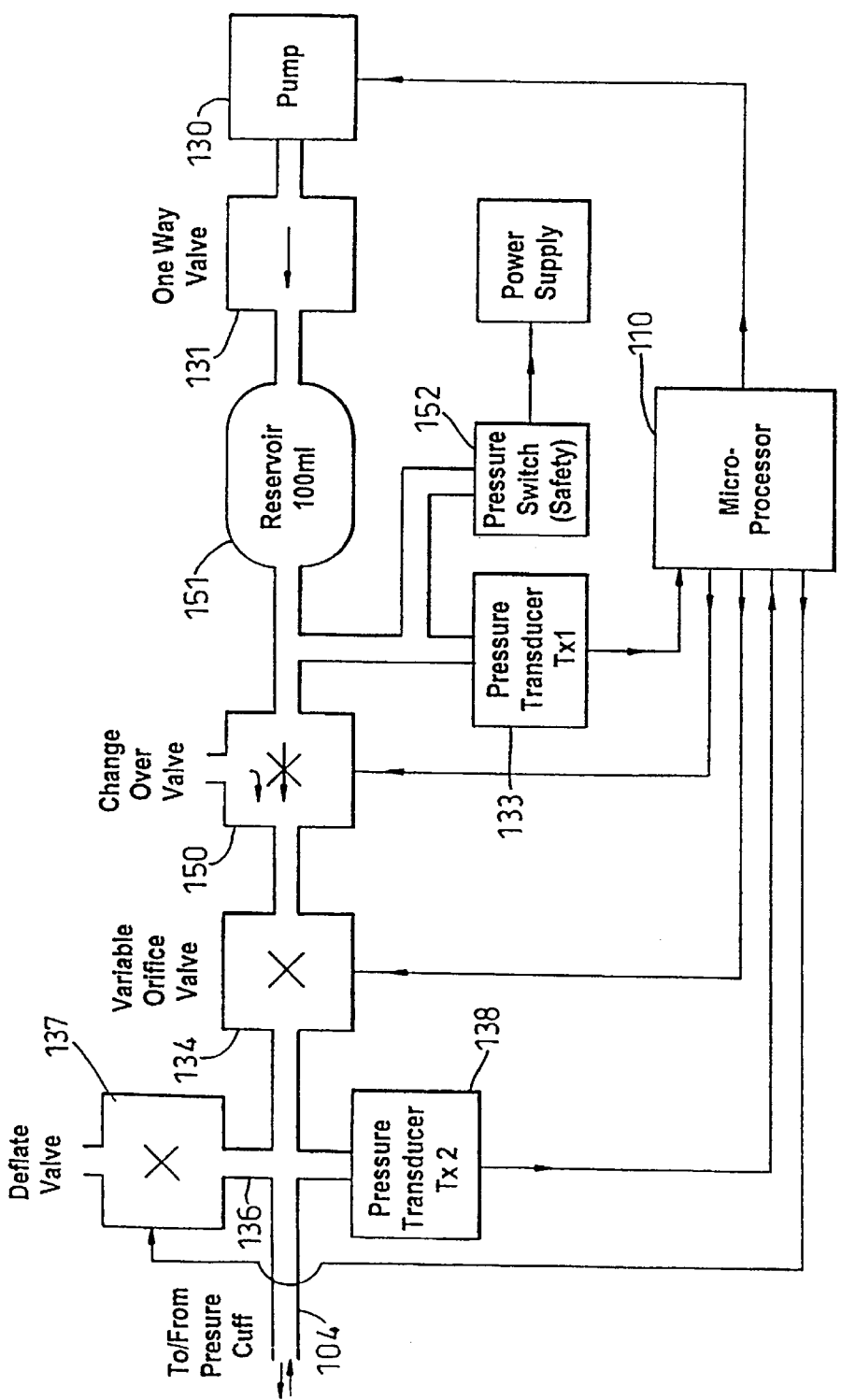
FIG. 11 shows a schematic block diagram illustrating pneumatic and control elements of an alternative non-invasive bladder pressure measurement system to that of FIGS. 1 and 2.

FIG. 10 summarises the data showing the correlation between data gathered simultaneously using a conventional urodynamics investigation technique and a cuff pressure test as described herein, for each of eight persons. The graph shows the isovolumetric bladder contraction pressure when the flow rate is reduced to zero (horizontal axis) and the cuff pressure required to reduce the flow to zero (vertical axis).

Urologists will be aware that the isovolumetric bladder contraction pressure measured with this technique will differ from the detrusor contraction pressure measured at peak flow rate. The detrusor pressure can be calculated by subtracting the abdominal pressure from the bladder pressure. From examination of recordings of 6 volunteers and 16 patients, the mean abdominal pressure is 39 cmH$_2$O with a standard deviation of 10. Another important difference is that, as predicted on theoretical grounds, higher pressure can be generated by the bladder when it is not emptying fluid. In practice this difference ranges from zero to approaching 100 cmH$_2$O, with most being around 20–30 cmH$_2$O. In the cases of unusually high increase, this is normally associated with a curved, more asymptotic approach to zero of the flow rate as tie cuff pressure rises. In the group of patients with obstruction, it is likely that they will be operating closer to their maximum before the cuff pressure is increased.

Some patients with obstruction have developed the habit of recruiting their abdominal muscles to try to assist with emptying the bladder. This is often self defeating as the pressure also applies to the urethra beyond the obstruction negating any benefit. In the measurement methods described above, this is readily apparent if it is occurring, because the flow rate recording is erratic. We have introduced the technique for such patients of asking them to count aloud while emptying the bladder. This makes it much more difficult for them to strain their abdominal muscles during the test which gives a more meaningful result. FIG. 7 discussed previously illustrates the use and benefit of this technique.

With reference to FIG. 10, there is shown an alternative pneumatic control system. Where items in this figure have the same or similar function to those indicated with reference to FIG. 2, the reference numerals are the same subject to the addition of one hundred, and will not be further described in any detail.

In the embodiment of FIG. 10, a single tube 104 is used to connect with the pneumatic cuff. This tube can be used for inflation/deflation functions as well as for measuring pressure, providing that a tube of sufficiently large internal diameter is used. In a preferred embodiment, the internal diameter of the tube is 2–3 mm.

A reservoir 151 is pressurised by the pump 130 and provides improved performance of the pressure control. A safety pressure switch 152 is provided to ensure that reservoir pressure (and hence pressure delivered to the cuff 2) does not exceed a safe value.

A variable orifice valve 134 is used to control inflation, allowing more flexible control and readily allowing either staircase or ramp inflation. A changeover valve 150 is provided to allow controlled deflation in addition to rapid deflation.

What is claimed is:

1. A method of making urethral pressure measurements on a male body comprising the steps of:
   (a) attaching a pneumatic cuff around the penis;
   (b) after commencement of urine flow through the penis, automatically inflating the cuff over a period of time in order to gradually occlude the urethra before voiding of the bladder is complete;
   (c) establishing a relationship between the urine flow and the cuff pressure applied; and
   (d) using said established relationship to determine a pressure measurement related to the urethral pressure under isovolumetric conditions.

2. A method according to claim 1 in which said urethral pressure measurement is used to deduce bladder pressure.

3. A method according to claim 1 in which the cuff is inflated in incremental steps over said period of time, with pressure and flow measurements being made between each increment.

4. A method according to claim 3 in which the incremental steps are applied at approximately 0.5 to 1.0 second intervals.

5. A method according to claim 3 in which the incremental steps are approximately 10 cmH$_2$O.

6. A method according to claim 1 further including the step of obtaining a series of measurements of the volume of urine passed over time, commencing at a low cuff pressure insufficient to cause significant reduction of urine flow and during the period of increasing cuff pressure until the urine flow has substantially ceased.

7. A method according to claim 6 further including the steps of:
   using said series of measurements to plot the relationship between cuff pressure and flow rate, and
   computing an intercept, from said series of measurements, with the cuff pressure axis to deduce an accurate value of cuff pressure when the flow rate is zero.

8. A method according to claim 7 further including the step of using said intercept value as a measure of the isovolumetric bladder contraction pressure.

9. A method according to claim 1 further including the steps of:
   deflating the cuff when the urine flow has been stopped; and
   repeating the steps (b) to (d) of claim 1 thereafter at least once.

10. A method according to claim 1 further including the steps of obtaining a series of measurements of the volume of urine passed over time, using said series of measurements to plot the relationship between cuff pressure and flow rate, and identifying a knee point on the relationship between cuff pressure and flow rate when the flow rate starts to fall.

11. A method according to claim 10 further including the step of sing said knee point as a measure of the minimum value for the bladder contraction pressure at maximum flow.

12. A method according to claim 10 further including the step of determining a pressure at the knee point as corresponding to the opening pressure of a compressive flow controlling zone.

13. A method according to claim 10 further including the step of identifying an intermediate point on the relationship at approximately 50% of flow rate value determined by said knee point, and using the cuff pressure value at said intermediate point as an empirical measurement relating bladder contraction to outlet function.

14. Apparatus for making urethral pressure measurements on a male body comprising:
   a pneumatic cuff adapted to fit around the penis;
   means for automatically inflating the cuff over a period of time during voiding of the bladder through the urethra in order to gradually occlude the urethra before voiding of the bladder is complete; and
   means for determining the cuff pressure at which the urethra becomes completely occluded.

15. Apparatus according to claim 14 further including means
   for recording volume of urine flow and cuff pressure as a function of time.

16. Apparatus according to claim 15 further including means to automatically inflate said cuff by incremental steps at a predetermined rate.

17. Apparatus according to claim 15 further including means for establishing, from said means for recording, a relationship between urine flow rate and cuff pressure and means for using said relation to determine isovolumetric bladder pressure.

18. Apparatus according to claim 17 further including means for automatically determining a knee point on the relationship between cuff pressure and flow rate when the flow rate starts to fall and outputting said knee point as a measure of the minimum value for the contraction pressure at maximum flow and as an estimate of the opening pressure of a compressive flow controlling zone.

19. Apparatus according to claim 17 further including means for automatically determining an intermediate point on the relationship at approximately 50% of flow rate value determined by said knee point, and outputting the cuff pressure value at said intermediate point as an empirical measurement relating bladder contraction to outflow function.

20. Apparatus for making urethral pressure measurements on a male body comprising:
   a pneumatic cuff adapted to fit around the penis;
   means for automatically inflating the cuff over a period of time during voiding of the bladder through the urethra in order to gradually occlude the urethra before voiding of the bladder is complete;
   means for recording volume of urine flow and cuff pressure as a function of time;
   means for establishing, from said means for recording, a relationship between urine flow rate and cuff pressure; and
   means for determining, from said relationship, information about the relationship between bladder contraction and outlet function.

21. Apparatus for making urethral pressure measurements on a male body comprising:
   a pneumatic cuff adapted to fit around the penis;
   means for automatically inflating the cuff over a period of time during voiding of the bladder through the urethra in order to gradually occlude the urethra before voiding of the bladder is complete;
   means for recording volume of urine flow and cuff pressure as a function of time;
   means for establishing, from said means for recording, a relationship between urine flow rate and cuff pressure; and
   means for determining, from said relationship, a measurement related to at least one of isovolumetric bladder pressure, a minimum value for the contraction pressure at maximum flow and opening pressure of a compressive flow controlling zone.

* * * * *